United States Patent
Wess et al.

[11] Patent Number: 5,178,136
[45] Date of Patent: Jan. 12, 1993

[54] LITHOTRIPTER INCLUDING A SAFETY DEVICE

[75] Inventors: Othmar Wess, Munich; Reiner Groezinger, Alling; Wolfgang Erhardt, Fuerstenfeldbruck, all of Fed. Rep. of Germany

[73] Assignee: Dornier Medizintechnik, Gemering, Fed. Rep. of Germany

[21] Appl. No.: 226,189

[22] Filed: Jul. 28, 1988

[30] Foreign Application Priority Data

Jul. 29, 1987 [DE] Fed. Rep. of Germany ....... 3725129

[51] Int. Cl.$^5$ .............................................. A61B 17/22
[52] U.S. Cl. .............................................. 128/24 CL
[58] Field of Search ......... 128/24 AA, 24 CL, 653 R, 128/662.03, 660.03

[56] References Cited

U.S. PATENT DOCUMENTS 3,942,531 3/1976 Hoff et al. ..................... 128/24 EL
4,811,725 3/1989 Grasser ........................... 128/24 EL Primary Examiner—Ruth S. Smith
Attorney, Agent, or Firm—R. H. Siegemund

[57] ABSTRACT

A medical treatment station which includes a medical treatment device such as a lithotripter including a liquid filled rotational ellipsoid as shockwave focussing chamber with a circular periphery and boundary and a liquid filled cushion e.g. bellows for coupling the treatment device to the body of a patient, the station further includes a rest or support for such a patient and structure for moving the treatment device and the rest in relation to each other, is improved by means a of safety device which includes a hollow, fluid-filled, elastic hose disposed along the periphery of the ellipsoid and inside the cushion; a pressure sensing transducer is coupled to the hose for sensing pressure therein including particularly any pressure increase if the periphery of the ellipsoid impacts upon another object such as said rest or support or the patient thereon so that the moving can safely be stopped.

2 Claims, 2 Drawing Sheets

LITHOTRIPTER INCLUDING A SAFETY DEVICE

BACKGROUND OF THE INVENTION

The present invention relates to improvements in a medical treatment station e.g. a lithotripter, and here particularly to the protection of a patient while situated on a rest or other suitable support in preparation for as well as during treatment with medical equipment for diagnostic and/or therapeutic purposes. The protection refers specifically to unwanted, undesired and unintended hitting of the patient by any movable and actually moving equipment which is to be positioned vis a vis the patient. The invention specifically relates to the art of lithotripsy, i.e. the comminution of concrements in the body of human beings by means of shock wave generators wherein a shock wave is to be produced in specific (geometric) relation to the patient so as to effect the comminution. Any positioning here requires that the equipment be moved in relation to a rest or support for the patient or that support with the patient on it be moved or both. Such relative motion conceivably occurs during different phases of the overall operation.

Broadly speaking, the situation is as follows. Lithotripsy, i.e. the comminution of concrements, is carried out in that the patient is placed on a rest or support or the like shown, for example, by Chaussy in his habilitation thesis, "extracorporeal shock wave lithotripsy, New aspects in the treatment of kidney stone disease", Karber Basel, München, New York etc. 1982, see also U.S. Pat. Nos. 4,705,026 and 4,669,483. The rest used in lithotripsy is positioned in physical, spatial relation to diagnostic or therapeutic equipment used for that purpose. The attending physician(s) or other medical personnel will provide for the proper positional adjustment, either manually or automatically through motor control, depending on the sophistication of the system involved. However, the situation is a delicate one. On the one hand, the positioning of the patient vis-a-vis the equipment or vice versa is the modality by means of which the focal point of concentrating shock waves is positioned in relation to the interior of a concrement to be comminuted which is, of course, inside the body of the patient and is visible only by x-ray or ultrasonics.

During positioning, physical impacting of the patient by the equipment must be avoided particularly in cases where adjustment is carried out through motor driven equipment; any changes in the position of the equipment must not cause undue pain to the patient upon engagement. It should be noted, however, that the equipment as it is being positioned is necessarily in physical contact with the body of the human. That contact is part of establishing a transmission path for shock waves which is so to speak spatially isolated and even though the equipment by necessity has to engage to be in contact with the patient's body there must by a physical isolation in the sense of avoiding accident producing impacts. The situation may seem to be not critical if the patient is already under anesthesia, but injury must be avoided of course and there is a tendency in the development of lithotripsy to reduce or do away entirely with the need for anesthesia, at least general anesthesia.

SUMMARY DESCRIPTION OF THE INVENTION

It is an object of the present invention to provide safety and security equipment which, independent of the state and condition of the patient and independent from the field of view of the attending physical or other medical personnel, will interrupt any relative motion between the equipment and the body of the patient when there is danger of injury to the patients body, pinching of the skin, or the like.

It is another object of the invention to provide a new and improved method and equipment for contactless comminution of concrements in human beings.

It is a further object of the invention to provide for the protection of patients from medical focusing equipment which is active in the interior of a human being and has to be positioned under different conditions.

It is a specific object of the present invention to provide a new and improved safety device and arrangement for patients placed on a rest or support, in particular, an arrangement or device, for example, for the comminution of concrements and including a liquid-filled focusing chamber, e.g. a rotational ellipsoid having a particular periphery that may come close to or even engage the skin of the patient. In addition, it is assumed that this focusing chamber and body of the patient are moved in relation to each other.

In accordance with the preferred embodiment of the present invention, the safety device and arrangement as per the specific object as well as the other objects is to include a hollow, fluid-filled, elastic preferably resilient member; preferably a hose is disposed along a periphery of the treatment equipment, the periphery being, e.g. circular nature in case the equipment includes a focusing chamber such as a rotational ellipsoid. This hose is contained in a coupler structure by means of which the focussing device and its liquidous interior is coupled to the patients body. The pressure in this fluid-filled member (hose) is measured whereby particularly any pressure increase is accurately monitored and instantly detected if occurring on account of the member impacting against another object such as the rest, support or the patient thereon. A switching structure is operated by the device sensing pressure for causing on such response any relative movement between the rest and the equipment to be interrupted.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DETAILED DESCRIPTION OF THE DRAWINGS

Figure 1:
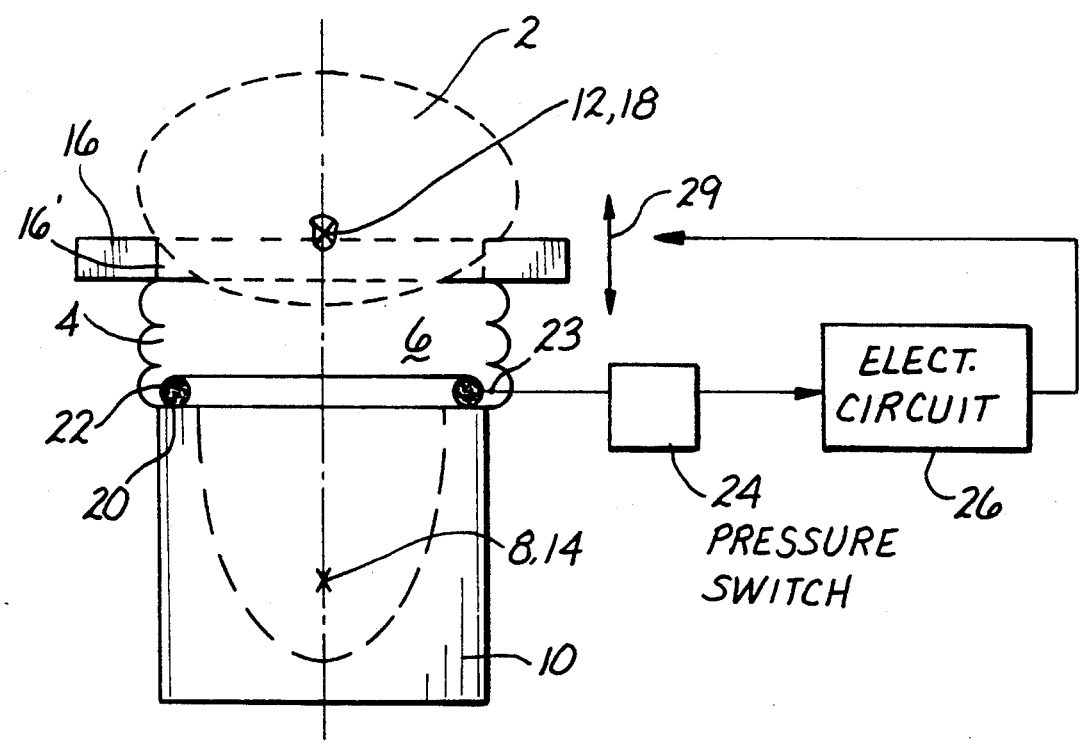
FIG. 1 is a somewhat schematic view of equipment to which the invention pertains, demonstrating a preferred embodiment for practicing the invention.

Proceeding now to the detailed description of the drawings, an application of shock waves for purposes of comminution of concrements in one or the other organ of a human body (2) is attained through equipment parts of which are shown in the drawings; as to further details, options and variations, please refer to the references of applicant's assignee mentioned above. However the present description is self sufficient for the purpose of practicing the invention. Basically, equipment of this kind refers to and includes a rest 16 on which the body of the patient 2 rests. the body 2 is exposed to shock-waves through an opening 16' in the rest 16.

These shock waves are generated by a source 14 such as a gap between electrodes and generating an underwater spark for purposes of causing a shock wave. This source 14 is situated in one focal point 8 of a rotational ellipsoid 10. The second focal point of the ellipsoid 10 is situated in a kidney stone. In other words, the equipment 10 and the body 2 assume appropriate positions in relation to each other. FIG. 1 illustrates these positions, of course, in a necessarily simplified manner as the shown symmetry is purely accidental and other positions may be expected.

The rotational ellipsoid 10 is filled with liquid, and a coupler cushion 4 in the form of bellows or the like establishes a transmission path through water from the source 14 of shock waves to the body of the patient being directly exposed to the interior of the cushion i.e. bellows 4 whose upper end may be attached to rest 16 and here particularly around opening 16' in the rest.

Figure 2:
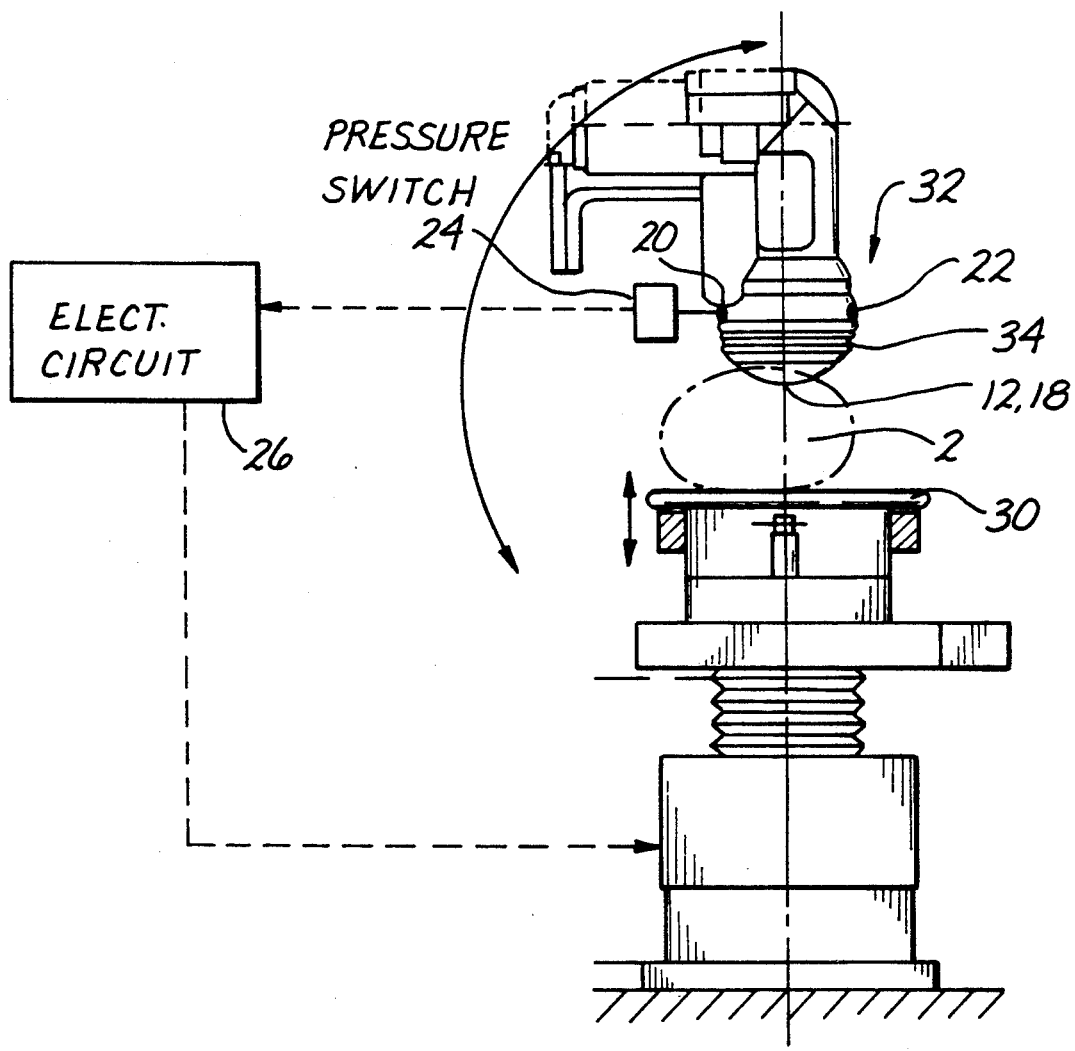
FIG. 2 illustrates a more elaborate incorporation of the equipment shown in FIG. 1 into equipment at large for the comminution of concrements.

In order to position the patient in relation to the shock wave producing equipment or vice versa it is necessary to shift the position of the rest 16 and the equipment 10 in relation to each other. For example, the equipment may be stationary as is schematically shown in FIG. 1 and the patient on the rest is being moved as the rest is being moved. A more sophisticated arrangement is shown in FIG. 2. Presently it is assumed that the rest 16 is moved indeed, for example, up and down and possibly also to the left or right. Further movement may permit positioning the rest back and forth in relation to equipment 10 specifically for the purpose of causing focal point 12 which is fixed in space to coincide with the concrement 18. However, the up and down movement is of principal interest here.

Speaking broadly, the concrement 18 is being positioned in relation to the focal point 12 through the basically 3-dimensional shifting of the rest 16. The up and down movement in this case means a production of a relative movement of the rest to and away from the ellipsoid and equipment 10 to position the body 2 of the patient in relation to the equipment 10 and here particularly to the edge 20 thereof. In the case of rather heavy patients and owing to a certain variety and possible positions as far as the concrement is concerned, it is possible that the body of the patient impacts on the edge 20.

It should be noted that of course one could inherently avoid this danger of impacting by choosing the rotational ellipsoid to be somewhat oblong, thus by inherently providing a sufficiently large spacing between the two focal points so that the device 10 could never impact upon the patient. However, the equipment parameters in this regard are determinative as far as optimizing the concentration of shock wave energy in this second focal point 12 is concerned. That, after all, is the principal purpose of the device. A compactness in geometry is highly instrumental in increasing the efficiency in this regard.

In order to avoid that the edge 20 of the equipment impacts on the patient's body, an annular elastic member is provided, i.e. a ring-shaped elastic hose 22 is arranged along the circle delineated by the surface 20. This hose is filled with gas or liquid. Normally the hose is fully inflated and it is assumed that pressure equilibrium occurs in the system.

If for some reason or other the bellows 4 in the vicinity of this hose 22 impacts on a part of the rest 16 of the body 2 of the patient or any other obstacle, the pressure will temporarily increase in that hose 22 as a result of a resilient reaction. It will bounce back shortly to average pressure; nevertheless at the moment of impact a peak in pressure obtains which is monitored by means of a transducer 23 being connected electrically to a pressure responsive switch 24. This pressure peak is translated into a switching operation that in turn is effective in a circuit 26 being an electronic circuit and being illustrated somewhat schematically. The circuit operates and includes driving equipment for moving the patient's rest up and down. Back and forth relative movement along the axes of the rotational ellipsoid is important because that motion is primarily responsible for an impact.

Therefore if there is a pressure peak that is monitored, switch 24 responds and causes circuit 26 to stop the motion along the arrow 29. This stoppage will avoid continuation of the collision motion of the rest, bed or support 16 with patient on it, in relation to the equipment 10. If this stopping proves to be an impediment in the sense that the focal point 12 of ellipsoid 10 cannot be placed in the concrement under the circumstances then a new adjustment has to be established, that is, the bellows for this case have to be shortened or a different rest has to be provided.

Measuring the pressure in the fluid of hose 22 is a measurement relative to the environment. This method avoids erroneous measurement in case there happens to be a drastic pressure change in the atmosphere. This is an aspect to be considered if in fact the response sensitivity for the transducer 23 is in the millibar range. A high degree of responsiveness is desirable simply to avoid or avert an unpleasant situation at the earliest possible moment.

As shown in FIG. 2, the safety equipment device in accordance with the invention is universally suitable for different kinds of coupling systems. FIG. 2 shows the body of the patient 2 on a motor driven rest 30. The shockwave treatment equipment 32 is in this case disposed above the patient; accordingly there is no opening or aperture in rest 30. Moreover, rest 30 is assumed to be movable up and down by operation of a post providing accurate positioning of the patient now in a vertical position. The treatment equipment is moveably disposed above the patient, basically for purposes of back and forth and rotational adjustment as indicated by the curved arrow. Coupling obtains here through a cushion 34, and the safety equipment (hose 22), broadly, is included in front of the rigid parts 20 of that equipment so that in this case there will be no collision with the body above if, for example, the cushion or bellow 34 no longer resiliently reacts. Otherwise, the equipment functions and operates in the manner outlined above.

The invention is not limited to the embodiments described above but all changes and modifications thereof, not constituting departures from the spirit and scope of the invention, are intended to be included.

we claim:

1. In a medical treatment station which includes a lithotripter having a liquid filled rotational ellipsoid for focussing shockwaves with a circular periphery and boundary and further having a liquid filled cushion means adapted for coupling the lithotripter to the body of a patient, the station further including a rest or support for such a patient, the station further including means for moving the lithotripter and the rest in relation to each other, the improvement comprising:

said cushion means including bellows a fluid-filled, elastic, resilient hose disposed along said periphery and inside said bellows;

means coupled to the hose for sensing pressure therein including the sensing of any pressure increase if the periphery of the ellipsoid impacts upon another object such as said rest or support or the patient thereon; and switch means connected to the means for sensing and to said means for moving, for interrupting any moving as provided by the means for moving when said means for sensing responds to an impact on the hose.

2. The improvement in a medical treatment station as in claim 1, said rest or support having an opening being aligned with said ellipsoid, said switch responding when the ellipsoid's periphery engages the rest at the opening thereof.

* * * * *